US005565319A

United States Patent [19]

Pedersen et al.

[11] Patent Number: 5,565,319
[45] Date of Patent: *Oct. 15, 1996

[54] ASSAY AND APPARATUS FOR DETECTING FELINE IMMUNODEFICIENCY VIRUS

[75] Inventors: Niels C. Pedersen, Winters; Janet K. Yamamoto, Davis, both of Calif.

[73] Assignee: The Regents of the University of California, Oakland, Calif.

[*] Notice: The term of this patent shall not extend beyond the expiration date of Pat. No. 5,118,602.

[21] Appl. No.: 226,447

[22] Filed: Apr. 12, 1994

Related U.S. Application Data

[63] Continuation of Ser. No. 832,201, Feb. 6, 1992, abandoned, which is a continuation of Ser. No. 614,474, Nov. 16, 1990, Pat. No. 5,118,602, which is a division of Ser. No. 89,700, Aug. 26, 1987, abandoned.

[51] Int. Cl.$^6$ ............................ C12Q 1/70; G01N 33/53; G01N 33/537; G01N 33/543
[52] U.S. Cl. .............................. 435/5; 435/7.92; 435/7.1; 435/7.95; 436/807; 530/387.1; 530/388.1
[58] Field of Search ............................ 435/5, 7.1, 7.92, 435/7.95; 436/504, 510, 807, 804; 530/387.1, 388.1

[56] References Cited

U.S. PATENT DOCUMENTS

| | | | |
|---|---|---|---|
| 4,520,113 | 5/1985 | Gallo et al. | 436/504 |
| 4,647,773 | 3/1987 | Gallo et al. | 435/239 |
| 4,652,559 | 3/1987 | Gallo et al. | 435/239 |
| 4,708,818 | 11/1987 | Montagnier et al. | 435/5 |
| 5,135,864 | 8/1992 | Montagnier et al. | 435/235.1 |
| 5,156,949 | 10/1992 | Luciw et al. | 435/5 |

FOREIGN PATENT DOCUMENTS 9013573  11/1990  WIPO ............................ C07K 13/00

OTHER PUBLICATIONS

Pedersen et al. 1986. The causes of false–positives encountered . . . J. Virol. Methods 14:213–228.
Lutz et al 1983a. Course of feline leukemia virus infection . . . Am. J. Vet. Res. 44(11):2054–59.
Lutz et al 1983 Monoclonal Antibodies to three epitopic regions . . . J. Immunol. Methods. 56:209–220.
Lutz et al. 1980. Humoral Immune Reactivity to Feline Leukemia . . . Cancer Res. 40:3642–51.
Marx et al. 1986 Prevention of Simian Acquired Immune Deficiency . . . J. Virol. 60(2):431–35.
Carlson et al. 1986. Evaluation of Three Commercial Screening Tests for AIDS . . . Am J. Clin. Pathol. 86:357–59.
Hunsmann et al. 1983. Active Immunization with Feline Leukemia . . . Med. Microbiol. Immunol. 171:233–41.
Hardy. 1987 In: Diseases of the Cat. Medicine & Surgery. ed. Holzworth. vol 1. pp. 246–268. W. B. Saunders Co.
Olmsted et al; "Nucleotide sequence analysis of F.I.V" PNAS, 86, pp. 8066–8092, 1989.

O'Connor et al. "Development and Evaluation of Immunoassay . . . FTLV" Jo Clin Microbiol, Mar. 1989, pp. 474–479.
Yamamoto et al; "Pathogenesis of experimentally induced FTLV"—Am J. Vet Res; 49(8) Aug. 1988.
Pedersen et al. (1987) Nature 235:790–793.
American Assoc. for Can. Res., May 23, 1987, Ab. No. 3337.
The 3rd Int'l. Conf. on AIDS, Jun. 1–5, 1987.
Fed. Amer. Soc. for Experimental Biology, Apr. 2, 1987.
Jarrett et al. (1964), Nature 202:306–307.
Rickard et al. (1969), Journal of the National Cancer Institute, 42:987–1004.
McKissick and Lamont (1970), Journal of Virology, 5:247–257.
Hoover et al. (1977), Journal of the National Cancer Institute, 58:443–444.
Fabricant (1977), American Journal of Veterinary Research, 38:1837–1842.
Hardy (1981), Journal of the American Animal Hospital Association, 17:981–997.
Pedersen et al. (1981), American Journal of Veterinary Research, 42:363–367.
Barre–Sinnousi et al. (1983), Science, 220:868–871.
Grant et al. (1984), Cancer Research, 44:498–502.
Gallo et al. (1984), Science, 224:500–502.
Hoshino et al. (1984), Int. J. Cancer, 34: 513–517.
Popovic et al. (1984), Science, 224:497–500.
Kanki et al. (1985), Science, 230:951–954.
Daniel et al. (1985), Science, 228:1201–1204.
Carlson et al. (1985), JAMA, 253:3405–3408.
Pedersen (1986) in *Diseases of the Cats*, Halsworth, ed., Saunders, Philadelphia, pp. 268–272.
Pedersen, et al., Clinical Overview of Feline Immunodeficiency Virus, JAVMA, vol. 199, No. 10, Nov. 15, 1991, pp. 1298–1305.
Olmsted, et al., Molecular Cloning of Feline Immunodeficiency Virus, Proc. Natl. Acad. Sci. USA, vol. 86, pp. 2448–2452, Apr. 1989 Medical Sciences.

(List continued on next page.)

*Primary Examiner*—James C. Housel
*Assistant Examiner*—N. M. Minnifield
*Attorney, Agent, or Firm*—Townsend and Townsend and Crew LLP

[57] ABSTRACT

Compositions derived from a novel viral isolate designated feline T-lymphotropic lentivirus (FTLV) include the whole virus; proteins, polypeptides and, polynucleotide sequences derived from the virus; and antibodies to antigenic sites on the virus. These compositions are useful in a variety of techniques for the detection of and vaccination against FTLV. Detection methods disclosed include immunoassays for both the virus and antibodies to the virus, and the use of polynucleotide probes to detect the viral genome. Vaccines include both wholly and partially inactivated viruses and subunit vaccines. Whole, live virus is also useful as a model system for predicting the behavior of human immunodeficiency virus (HIV).

10 Claims, 2 Drawing Sheets

OTHER PUBLICATIONS

Pederson, et al., Isolation of a T–Lymphotropic Virus from Domestic Cats With an Immunodeficiency–Like Syndrom, Science, vol. 28, 13 Feb. 1987, pp. 790–793.

Marx, et al., Prevention of Simian Acquired Immune Deficiency Syndrome With a Formalin–Inactivated Type D Retrovirus Vaccine, Jor. of Virology, vol. 60, No. 2, Nov. 1986, pp. 431–435.

Benveniste, et al., Isolation of a Lentivirus from a Macaque W/Lymphoma: Comparison w/ HTLV–III/LAV and Other Lentiviruses, Jor. of Virology, vol. 60, No. 2, Nov. 1986, pp. 483–490.

Carlson, et al., Evaluation of Three Commercial Screening Tests for AIDS Virus Antibodies, A.J.C.P., vol. 86, No. 3, Sep. 1986, pp. 357–359.

Baskin, et al., Transmissible Lymphoma and Simian Acquired Immunodeficiency Syndrome in Rhesus Monkeys, Jnci, vol. 77, No. 1, Jul. 1986, pp. 127–139.

Haase, Pathogenesis of Lentivirus Infections, Nature, vol. 322, 10 Jul. 1986, pp. 130–136.

Coffin, et al., Letter re Human Immunodeficiency Viruses, Science, vol. 232, 9 May 1986, p. 697.

Maul, et al., Pathogenesis of Simian AIDS in Rhesus Macaques Inoculated with the SRV–1 Strain of Type D Retrovirus, Am. J. Vet. Res., vol. 47, No. 4, Apr. 1986, pp. 863–868.

Mullins, et al., Letter re Disease–Specific and Tissue–Specific Production of Unintegrated Feline Leukaemia Virus Variant . . . , Nature, vol. 319, 23 Jan. 1986, pp. 333–336.

Specter, et al., *Clinical Virology Manual*, Published by Elsevier Science Publishing Company, Inc., New York, 1986, Chap. 3, Primary Isolation of Viruses, pp. 31–51.

Kanki, et al., Isolation of T–Lymphotropic Retrovirus Related to HTLV–III/LAV from Wild–Caught African Green Monkeys, Science vol. 230, 22 Nov. 1985, pp. 951–954.

Barlough, et al., Effect of Recent Vaccination on Feline Coronavirus Antibody Test Results, Feline Practice, vol. 15, No. 5, Sep.–Oct. 1985, pp. 17–26.

Carlson, et al., Aids Serology Testing in Low– and High- –Risk Groups, JAMA, vol. 253, No. 23, Jun. 21, 1985, pp. 3405–3408.

Daniel, et al., Isolation of T–Cell Tropic HTLV–III–Like Retrovirus from Macaques, Science, vol. 228, 7 Jun. 1985, pp. 1201–1204.

Nathanson, et al., Experimental Visna in Icelandic Sheep: The Prototype Lentiviral Infection, Reviews of Infectious Diseases, vol. 7, No. 1, Jan.–Feb. 1985, pp. 75–82.

Cheevers, et al., Equine Infectious Anemia Virus: Immunopathogenesis and Persistence, Reviews of Infectious Diseases, vol. 7, No. 1, Jan.–Feb. 1985, pp. 83–88.

Gonda, et al., Sequence Homology and Morphologic Similarity of HTLV–III and VISNA Virus, A Pathogenic Lentivirus, Science, vol. 227, 11 Jan. 1985, pp. 173–177.

Munn, et al., Ultrastructural Comparison of the Retroviruses Associated With Human and Simian Acquired Immunodeficiency . . . , Lab. Invest., vol. 53, No. 2, 1985, pp. 194–199.

Fields, et al., *Virology*, Published by Raven Press, New York, 1985, Chapter 1, Intro. to Animal Virology, pp. 1–5, and Chapter 58, Human T–Cell Leukemia Viruses, pp. 1345–1371.

Freeman, *Textbook of Microbiology*, Pulished by W. B. Saunders Company, 1985, pp. 730–734.

Kucera, et al., *Fundamentals of Medical Virology*, Published by Lea & Febiger, Philadelphia, 1985, Ch. 2, Growth and Assay of Viruses, pp. 16–26, Ch. 24, Priciples of Lab Diagnosis, p. 195.

Pedersen, Feline Syncytium–Forming Virus Infection, Viral Diseases, pp. 268–272, Undated (last reference 1984).

Gravell, et al., Transmission of Simian Acquired Immunodeficiency Syndrome (SAIDS) with Type D Retrovirus Isolated . . . , Proc. of Soc. for Ex. Bio. & Med., 177, 1984, pp. 491–494.

Hoshino, et al., Immortalization of Peripheral Blood Lymphocytes of Cats by Human T–Cell Leukemia Virus, Int. J. Cancer, 34, 1984, pp. 513–517.

Levy, et al., Isolation of Lymphocytopathic Retroviruses from San Francisco Patients with AIDS, Science, vol. 225, 20 Jun. 1984, pp. 840–842.

Popovic, et al., Detection, Isolation, and Continuous Production of Cytopathic Retroviruses (HTLV–III) from Patients w/ . . . , Science, vol. 224, 4 May 1984, pp. 497–500.

Schupbach, et al., Serological Analysis of a Subgroup of Human T–Lyphotropic Retroviruses (HTLV–III) Associated with AIDS, Science, vol. 224, 4 May 1984, pp. 503–505.

Bouillant, et al., Ultrastructural Comparison of Oncovirinae (Type C), Spumavirinae, and Lentivirinae: Three Subfamilies . . . , Jnci., vol. 72, No. 5, May 1984, pp. 1075–1079.

Gallo, et al., Frequent Detection and Isolation of Cytopathic Retroviruses (HTLV–III) from Patients w/ AIDS and At Risk . . . Science, vol. 224, 4 May 1984, pp. 500–502.

Sarngadharan, et al., Antibodies Reactive w/ Human T–Lymphotropic Retroviruses (HTLV–III) in the Serum of Patients With . . . Science, vol. 224, 4 May 1984, pp. 506–508.

Fine, Transmission of Simian AIDS With Type D Retroviruse Isolate, The Lancet, Feb. 11, 1984, pp. 334–335.

Grant, et al., Comparison of Feline Leukemia Virus–Infected and Normal Cat T–Cell Lines in Interleukin 2–Conditioned . . . Cancer Research 44, Feb. 1984, pp. 498–502.

Belshe, *Textbook of Human Virology*, Published by PSG Publishing Co., Littleton, MA, Chp. 2, Intro to Methods for Characterizatn of Viruses and Viral Macromolecules, pp. 29–37.

London, et al., Experimental Transmission of Simian Acquired Immunodeficiency Syndrome (SAIDS) and Kaposi–Like Skin Lesions, The Lancet, Oct. 15, 1983, pp. 869–873.

Gottlieb, The Acquired Immunodeficiency Syndrome, Annals of Internal Medicine, 1983, vol. 99, pp. 208–220.

Curran, et al., Epidemic Acquired Immune Deficiency Syndrome: Epidemiologic Evidence for a Transmissible Agent, JNCI, vol. 71 No. 1, Jul. 1983, pp. 1–4.

Barre–Sinoussi, et al., Isolation of a T–Lymphotropic Retrovirus from a Patient At Risk for Acquired Immune Deficiency . . . Science, vol. 220, 20 May 1993, pp. 868–871.

Popovic, et al., Isolation and Transmission of Human Retrovirus (Human T–Cell Leukemia Virus), Science, vol. 219, 18 Feb. 1983, pp. 856–859.Pedersen, et al., A Transient Febrile "Limping" Syndrome of Kittens Caused By Two Different Strains of Feline Calicivirus, Feline Practice, vol. 13, No. 1, Jan.–Feb. 1983, pp. 26–34.

Lutz, et al., Monoclonal Antibodies to Three Epitopic Regions of Feline Leukemia Virus p27 and Their Use Ni Enzyme–Linked . . . Jor. of Immun. Methods, vol. 56, 1983, pp. 209–220.

Centers for Disease Control, MMWR, Dec. 10, 1982, pp. 652–654.

Centers for Disease Control, MMWR, May 21, 1982, vol. 31, No. 19, pp. 249–251.

Centers for Disease Control, Special Report—Epidemiological Aspects of the Current Outbreak of Kaposi's Sarcoma and Opp . . . New England Jor. of Med., vol. 306, No. 4, Jan. 28, 1982, p. 248.

Hardy, The Feline Sarcoma Viruses, Jor. of the Am. Animal Hospital Assoc., vol. 17, Nov./Dec. 1981, pp. 981–997.

Swanstrom, et al., Interaction of Psoralen Derivatives with the RNA Genome of Rous Sarcoma Virus, Virology, vol. 113, 1981, pp. 613–622.

Rho, et al., Characterization of the Reverse Transcriptase from a New Retrovirus (HTVL) Produced By a Human Cutaneous T–Cell . . . Virology, vol. 112, 1981, pp. 355–360.

Pedersen, et al., Infection Studies in Kittens, Using Feline Infectious Peritonitus Virus Propagated in Cell Culture, Am. Jor. of Veternary Research, vol. 42, No. 3, pp. 363–367.

Lutz, et al., Humoral Immune Reactivity to Feline Leukemia Virus and Associated Antigens In Cats Naturally Infected W/ . . . Cancer Research, vol. 40, Oct. 1980, pp. 3642–3651.

Poiesz, et al., T–Cell Lines Established from Human T–Lymphocytic Neoplasias By Direct Response to T–Cell Growth Factor, Medical Sciences, Jun. 16, 1980, pp. 6815–6819.

Colcher, et al., Purification and Characterization of the RNA–Directed DNA Polymerase of a Primate Type–D Retrovirus: Mason . . . Biochimica et Biophysica Acta, vol. 607, 1980, pp. 445–456.

Cork, et al., The Pathogenesis of Viral Leukoencephalomyelitis–Arthritis of Goats, Laboratory Investigation, vol. 42, No. 6, 1980, pp. 596–602.

Popovic, et al., Detection of Viral Markers and Incomplete Viral Genome Rescue from ASV Transformed Rodent Cells, Folia Biologica (Praha), vol. 26, 1980, pp. 244–260.

Towbin, et al., Eletrophoretic Transfer of Proteins from Polyacrylamide Gels to Nitrocellulose Sheets: Procedure and Some . . . Proc. Natl. Acad. Sci. USA, vol. 76, No. 9, Sep. 1979, p. 4350.

Barre–Sinoussi, et al., Enhancement of Retrovirus Production by Anti–Interferon Serum, Ann. Microbiol., 1979, 130 B, pp. 349–362.

Grant, et al., Analysis of Feline Lymphoma Cells by Complement–Dependent Antibodies in Feline Leukemia Virus Contact Cats . . . J. Natl. Cancer Inst., vol. 60, No. 1, Jan. 1978, pp. 161–166.

Fabricant, Herpesvirus–Induced Urolithiasis in Specific-–Pathogen–Free Male Cats, Am. J. Vet. Res., vol. 38, No. 11, Apr. 4, 1977, pp. 1837–1842.

Essex, et al., Horizontal Transmission of Feline Leukemia Virus Under Natural Conditions in a Feline Leukemia Cluster Household Int. J. Cancer, vol. 19, Jul. 29, 1977, pp. 90–96.

Raamsdonk, et al., Detection of Antigens and Antibodies by an Immuno–Peroxidase Method Applied on Thin Longitudinal . . . Jor. of Immuno. Methods, vol. 17, Apr. 25, 1977, pp. 337–348.

Popovic, et al., Expression of Viral Protein P27 in Avian Sarcoma Virus–Transformed Mammalian Cells and Helper-–Depen . . . Int. J. Cancer, vol. 19, Apr. 4, 1977, pp. 834–842.

Hoover, et al., Brief Communication: Horizontal Transmission of Feline Leukemia Virus Under Experimental Conditions, J. Natl. Cancer Inst., vol. 58, No. 2, Feb. 1977, pp. 443–444.

Hughes, The Virus—A History of the Concept, published 1977 by Heinemann Ed. Books, London, Chp. 5, The Development of the Microbial and Nonmicrobial Concepts . . . , pp. 61–95, 389–403.

Sparger, et al., Feline Immunodeficiency Virus Infection, pp. 530–534, Undated (last reference 1988).

Morgan, et al., Selective In Vitro Growth of T Lymphocytes from Normal Human Bone Marrows, Science, vol. 193, 10 Sep. 1976, pp. 1007–1008.

Petursson, et al., Pathogenesis of VISNA—I. Sequential Virologic, Serologic, and Pathologic Studies, Lab. Investigation, vol. 35, No. 4, pp. 1976.

Palsson, Maedi and Visna in Sheep, published by North-–Holland Publishing Co., 1976, Chp. 2, pp. 17–43.

Fenner, Classification and Nomenclature of Viruses, published by S. Karger, 1976, pp. 1–105.

Boothe, et al., Ultrastructural Studies of a Visna–Like Syncytia–Producing Virus from Cattle with Lymphocytosis, Jor. of Virology, Jan. 1974, vol. 13, No. 1, pp. 197–204.

Fenner, et al., The Biology of Animal Viruses, published by Academic Press, 1974, Chp. 2, Cultivation, Assay and Analysis of Viruses, pp. 35–71.

Essex, Horizontally and Vertically Transmitted Oncornaviruses of Cats, pp. 176–249, Undated (last reference 1974).

Abrell, et al., Purification, Characterization, and Comparison of the DNA Polymerase from Two Primate RNA Tumor Viruses, Jor. of Virology, vol. 12, No. 3, Sep. 1973, pp. 431–439.

Hardy, et al., Horizontal Transmission of Feline Leukaemia Virus, Nature, vol. 244, Aug. 3, 1973, pp. 266–269.

Fischinger, et al., Isolation of an RD–114–Like Oncornavirus from a Cat Cell Line, Jor. of Virology, vol. 11, No. 6, Jun. 1973, pp. 978–985.

Jarrett, et al., Horizontal Transmission of Leukemia Virus and Leukemia in the Cat, J. Natl. Cancer Inst., 51: 833–841, 1973.

Hardy, et al., Detection of the Feline Leukemia Virus and Other Mammalian Oncornaviruses by Immunofluorescense, Unifiy. Concept of Leuk. Bibl. Haemat, No. 39, 1973, pp. 778–799.

Scolnick, et al., Immunological Characterization of Primate C–Type Virus Reverse Transcriptases, Nature New Biology, vol. 235, Jan. 12, 1972, pp. 35–40.

Anderson, et al., Feline Leukemia–Virus Infection of Kittens: Mortality Associated with Atrophy of the Thymus and Lymphoid . . . Jor. of Natl. Cancer Inst., vol. 47, No. 4, Oct. 1971, pp. 807–817.

Temin, et al., Viral RNA–Dependent DNA Polymerase, Nature, vol. 226, Jun. 27, 1970, pp. 1209–1213.

McKissick, et al., Characteristics of a Virus Isolated from a Feline Fibrosarcoma, Jor. of Virology, vol. 5, No. 2, Feb. 1970, pp. 247–257.

Rickard, et al., A Transmissible Virus–Induced Lymphocytic Leukemia of the Cat, Jor. of the Natl. Cancer Inst., vol. 42, No. 6, Jun. 1969, pp. 987–1014.

Svoboda, et al., Rescue of Rous Sarcoma Virus from Virogenic Mammalian Cells Associated with Chicken Cells and Treated . . . J. Gen. Virol, 1969, vol. 4, pp. 523–529.

Maramorosch, et al., Methods in Virology, published by Academic Press, 1967, vol. 1, Chp. 6, Lab. Methods of Virus Transmission in Multicellular Organisms, pp. 163–235.

Boyum, Isolation of Mononuclear Cells and Granulocytes from Human Blood, Norwegian Defence Res. Establishment, Paper IV, pp. 77–89, Undated (last reference 1966).

Snyder, et al., Transmissible Feline Fibrosarcoma, Nature, vol. 221, Mar. 15, 1969, pp. 1074–1075.

Jarrett, et al., Leukaemia in the Cat, Nature, vol. 202, May 9, 1964, pp. 566–567.

Jarrett, et al., A Virus–Like Particle Associated with Leukaemia (Lymphosarcoma), Nature, vol. 202, May 9, 1964, pp. 567–568.

Svoboda, Malignant Interaction of Rous Virus with Mammalian Cells In Vivo and In Vitro, Intrnatl. Conf. on Avian Tumor Viruses, Natl. Cancer Inst. Monograph 17, Dec. 1964, pp. 277–298.

Young, *Witton's Microbiology*, published by The Blakiston Div., 1961, Chp. 36, Filtrable Viruses: General Char.; Bacterial . . . pp. 428–442.

Taliaferro, *The Journal of Infectious Diseases*, published by Univ. of Chicago, 1953, Transmission Experiments with Maedi, pp. 166–175.

Sigurdsson, RIDA, a Chronic Encephalitis of Sheep with General Remarks on Infections Which Develop . . . , Special Univ. Lectures of Univ. of London, Mar. 1954, pp. 341–354.

Steinhardt, et al, Studies on the Cultivation of the Virus of Vaccinia, received for publication Jun. 9, 1913, pp. 294–300.

Zook, et al., Ultrastructural Evidence for the Viral Etiology of Feline Infectious Peritonitis, Path. vet. 5:91–95 (1968).

Sigurdsson, et al., VISNA, a Demyelinating Transmissible Disease of Sheep*, from the Institute for Experimental Pathology, Univ. of Iceland, Keldur, Reykjavik, pp. 389–403.

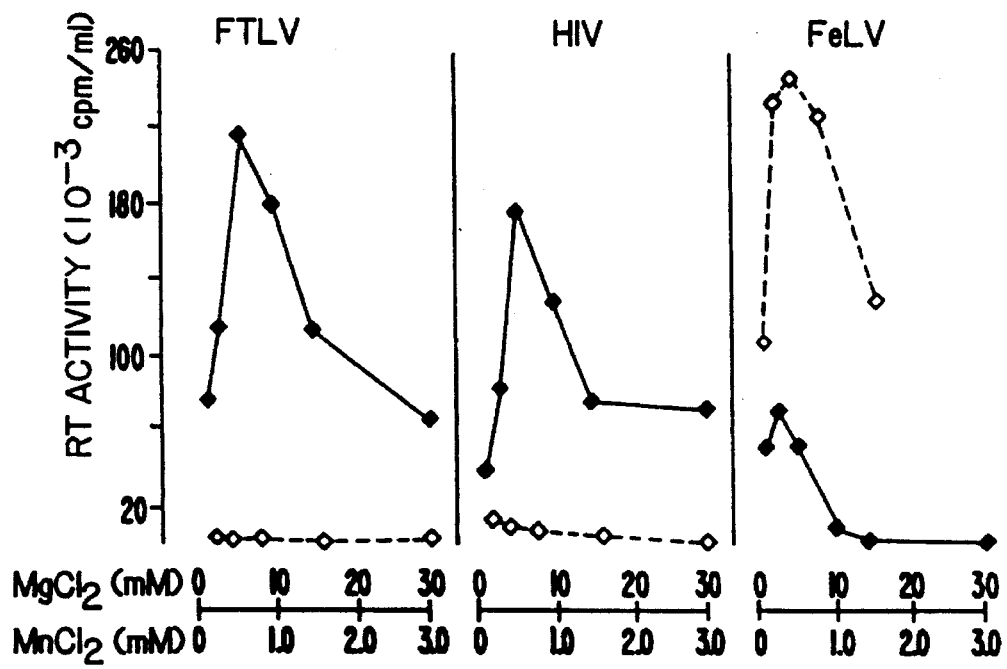
FIG. 1A FIG. 1B FIG. 1C
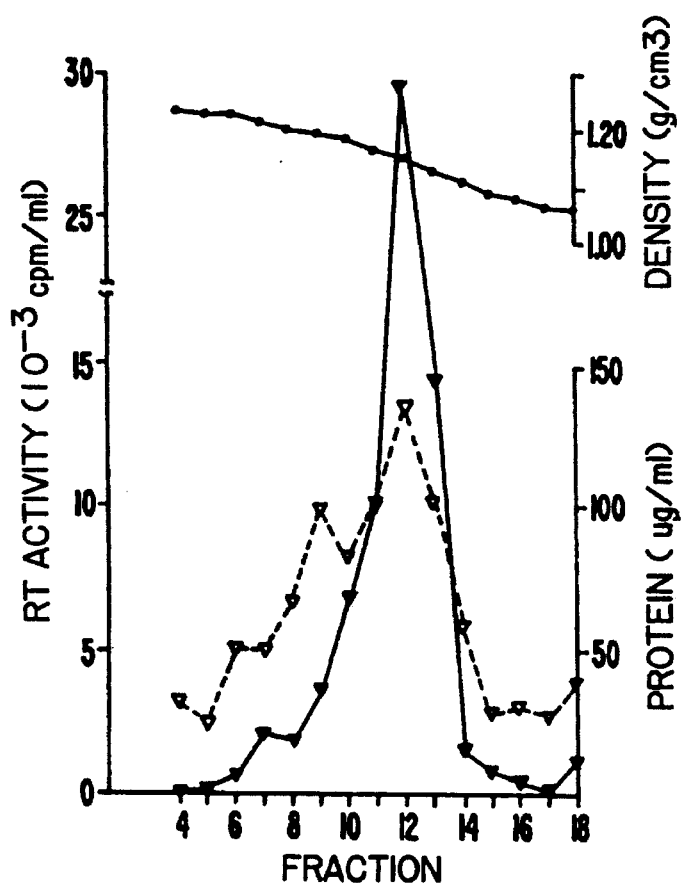
FIG. 3

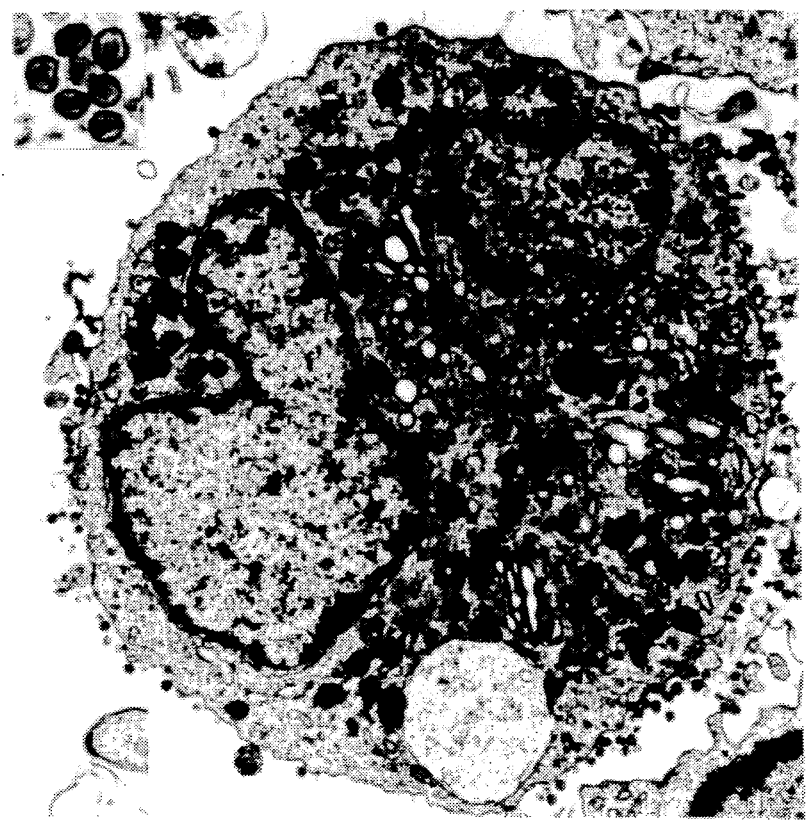
FIG.2
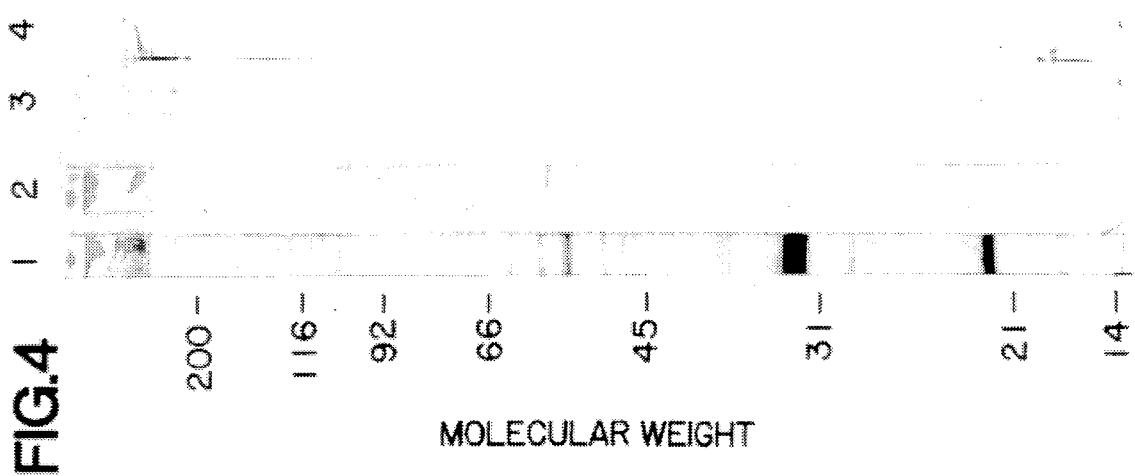
FIG.4 MOLECULAR WEIGHT

ASSAY AND APPARATUS FOR DETECTING FELINE IMMUNODEFICIENCY VIRUS

This is a Continuation of application Ser. No. 07/832,201, filed Feb. 6, 1992, now abandoned, which is a Continuation of U.S. Ser. No. 07/614,474; filed Nov. 16, 1990, now U.S. Pat. No. 5,112,602 which is a Divisional of U.S. Ser. No. 07/089,700; filed Aug. 26, 1987, now abandoned.

BACKGROUND OF THE INVENTION

1. Field of the Invention

The present invention relates generally to the detection and treatment of viral infection. More particularly, the invention relates to compositions and methods useful for the diagnosis of and vaccination against infection with a newly-discovered lymphotropic retrovirus, designated feline T-lymphotropic lentivirus, more recently designated feline immunodeficiency virus (FIV).

Domestic cats may become infected with several retroviruses, including feline leukemia virus (FeLV), feline sarcoma virus (FeSV), endogenous type C oncornavirus (RD-114), and feline syncytia-forming virus (FeSFV). Of these, FeLV is the most significant pathogen, causing diverse symptoms, including lymphoreticular and myeloid neoplasms, anemias, immune-mediated disorders, and an immunodeficiency syndrome which is similar to human acquired immune deficiency syndrome (AIDS). Recently, a particular replication-defective FeLV mutant, designated FeLV-FAIDS, has been more particularly associated with immunosupressive properties.

While immunodeficiency syndrome in cats has normally been associated with FeLV, immunodeficiency-like symptoms have been observed in cats which are seronegative for FeLV, usually without alternative explanation. It would be desirable to identify etiological agents other than FeLV which are responsible for causing immunodeficiency in cats. It would be particularly desirable to provide methods and compositions for the detection of and vaccination against such newly-identified etiological agents.

2. Description of the Background Art

The discovery of feline T-lymphotropic lentivirus was first reported in Pedersen et al. (1987) Science 235:790–793. Abstracts concerning the discovery of the virus have been presented at the American Association for Cancer Research on May 23, 1987 (Abstract No. 3337); and The Third International Conference on Acquired Immune Deficiency Syndrome, Jun. 1–5, 1987. A poster concerning discovery of the virus was presented at a meeting of the Federation of American Society for Experimental Biology on Apr. 2, 1987.

SUMMARY OF THE INVENTION

Compositions and methods are provided for detection of and vaccination against a novel feline retrovirus designated feline T-lymphotropic lentivirus (FTLV), more recently designated feline immunodeficiency virus (FIV). The compositions include the whole virus and portions thereof, particularly including polypeptides which are cross-reactive with antibodies specific for determinant sites characteristic of the virus, such as those found on the major envelope and core proteins. The compositions further include antibodies capable of reacting with the virus and polynucleotides which are capable of duplexing with the FTLV genome. The FTLV virus will also serve as a useful model for other mammalian retroviruses, particularly the human immunodeficiency virus (HIV) responsible for acquired immunodeficiency syndrome (AIDS), Using the compositions of the present invention, the virus and viral infection may be detected by a variety of techniques, particularly immunoassays and techniques employing nucleotide probes. Immunoassays provide for the detection of the virus or antibody to the virus in a physiological specimen, particularly blood and lymph tissue. Nucleotide probes are used to detect the presence of the FTLV genome in a physiological specimen. Vaccines may be prepared from the whole virus, either by partial or complete inactivation. Alternatively, subunit vaccines may be prepared from antigenic portions of the viral proteins.

BRIEF DESCRIPTION OF THE DRAWINGS

FIGS. 1A–1C demonstrates the $Mg^{+2}$-dependent (♦) and $Mn^{+2}$-dependent (◊) reverse transcriptase (RT) activity and culture fluids containing FTLV, HIV, and FeLV. FeLV-producer line, FL-74, and HIV-infected H9 cells, were clarified by centrifugation at 3,000 rpm for two hours. Portions of cell-free fluids (1 ml) were centrifuged at 17,000 rpm for one hour, and the virus pellets were assayed for RT activity. Conditions of the assay are described in the Experimental Section hereinafter.

FIG. 2 is a transmission electron micrograph of a lymphocyte culture infected with FTLV. Extracellular viral particles surrounding a T-lymphocyte (center, ×25,000) and a budding particle from a T-lymphocyte (left inset, ×80,000). Mature virions were ellipsoid (120×150 nm) in shape with typical lentivirus-type nucleocapsids (right inset, ×80,000).

FIG. 3 illustrates the sucrose density gradient banding of FTLV. Virus was concentrated from T-lymphocyte culture supernatants by low speed centrifugation to remove subcellular debris and ultracentrifugation to pellet the virion particles. Pelleted virions were then layered on a 10/50% (W/V) continuous sucrose gradient in tris-base (pH 7.4) containing 0.1M NaCl and 1 mM EDTA, and centrifuged in a Beckman SW41 rotor for three hours at 36,000 rpm. Fractions (0.5 ml) were collected from the bottom of the gradient and assayed for RT activity (▼), protein concentration (▽), and density (●). The purification procedure yielded 1 milligram of FTLV per liter of T-lymphocyte culture.

FIG. 4 is Western blot of FTLV-infected cell lystate with lane 1 derived from a serum sample from cat 2429, lane 2 derived from a serum sample of an antibody-negative SPF cat, lane 3 derived from pooled serum samples from HIV-positive humans, and lane 4 derived from pooled serum samples from HIV-negative humans. The bands which appear in lane 1 indicate the presence of proteins in FTLV which appear to correspond to the major core protein p24, gag precursor protein p55, and endonuclease protein p32 of HIV, or cellular HLA-D12 p32.

DESCRIPTION OF THE SPECIFIC EMBODIMENTS

A novel virus designated feline T-lymphotropic lentivirus (FTLV), more recently designated feline immunodeficiency virus (FIV), has been discovered and isolated in substantially pure form. The virus is infectious in cats, causing a wide variety of symptoms, including abortion, alopecia, anemia, chronic rhinitis, conjunctivitis, diarrhea, emaciation, enteritis, gingivitis, hematochezia, neurologic abnormalities, periodontitis, and seborrheic dermititis. The course of the disease is usually fatal.

The etiology, pathogenesis, and morphology of FTLV closely resemble those of human immunodeficiency virus (HIV) and simian T-lymphotropic virus III (SAIDS), which cause acquired immunodeficiency syndrome in humans and primates, respectively. FTLV does not appear to be antigenically related to HIV or to SAIDS, but rather appears to be a species-adapted lentivirus that has existed in cats for some time. Preliminary surveys conducted by the inventors herein indicate that FTLV infection in cats may be widespread, possibly accounting for a significant proportion of the immunodeficiency symptoms found in cats who are free from FTLV infection.

FTLV is a feline immunodeficiency virus characterized as a retrovirus, more specifically as a lentivirus, which is tropic for T-lymphocytes of the host which it infects. The virus is also characterized by horizontal transmission, and may further be characterized by vertical transmission in at least some cases.

It is expected that FTLV is polymorphic, and reference to FTLV in the present application is intended to encompass the entire FTLV family, including a variety of strains which share substantial amino acid sequence and nucleotide sequence homology and which are immunologically related. Substantial amino acid sequence homology means at least about 75% homology, usually at least about 80% homology, and frequently 90% homology and above in at least some of the viral genes and proteins. For example, the env, gag, or pol regions may display the requisite homology, while the genome as a whole does not. In such cases, so long as the viruses are immunologiically related, the viruses will be considered to be FTLV within the scope of the present invention.

By immunologically related it is meant that the various strains will display substantial serologic cross-reactivity with the newly-discovered strain which has been deposited. Serologic cross-reactivity is defined as the ability of an antiserum or antibodies specific for the deposited FTLV strain to react with other FTLV strains as well as the deposited strain. Usually, immunologically related strains will cross-react with antibodies specific for more than one epitopic site, usually more than five epitopic sites, and frequently ten or more epitopic sites.

Conveniently, FTLV strains may be identified by Western blot analysis where purified virus is disrupted with a suitable detergent, e.g., sodium dodecyl sulfate, and separated on a slab gel by electrophoresis. The separated polypeptide bands are transferred from the gel to nitrocellulose filter paper and visualized with labelled antibody. The molecular weights of the various resolved bands may then be determined by comparison to known molecular weight standards. Substantial similarity between the Western blot analysis of an unidentified virus and that of a known FTLV virus indicates that the unknown virus is likely an FTLV virus.

FTLV encodes an RNA-dependent DNA polymerase (reverse transcriptase) which is $Mg^{+2}$-dependent with maximal activity occurring at a $Mg^{+2}$ concentration of approximately 5 mM and pH of approximately 7.8. FTLV bands at a density of about 1.15 $gcm^3$ in a continuous sucrose gradient. Western blotting of FTLV-infected cell lysate yields major bands at approximately 22 to 26 kD, usually about 24 kD; 50 to 60 kD, usually about 55 kD; and 28 to 36 kD, usually about 32 kD.

FTLV may be isolated from the sera of infected cats by conventional techniques. For example, peripheral blood lymphocytes (PBL) may be isolated from the blood of infected cats and placed in suitable culture media. The cultures are incubated, with normal PBL's being periodically introduced to the culture in order to maintain its viability as the original cells are killed by the virus. The infected cells should be placed in fresh culture medium periodically, and the virus may be recovered from the supernatant of the cell culture by sucrose-gradient separation, or other known separation techniques.

The FTLV may also be obtained from other specimens, particularly from the lymph tissues of infected animals. The lymph tissues are broken and then suspended in culture medium, and the procedures described above are then carried out.

Compositions according to the present invention include the whole virus, as well as portions of the virus. The whole virus may be maintained in in vitro culture, as described above, or may be viably frozen at a temperature at or below about −78° C. (solid $CO_2$-dry ice), usually in the presence of agents which promote amorphous, vitreous solidification rather than crystallization. Suitable agents include glycerol and dimethylsulfoxide. Portions of the FTLV of particular interest include the structural and regulatory proteins encoded by the FTLV genome, including the envelope and core proteins, and fragments thereof.

Polypeptides of the present invention will be either haptenic or antigenic, including at least six amino acids, usually at least nine amino acids, and more usually twelve or more amino acids found contiguously within one of the natural FTLV proteins. Polypeptides will generally correspond to at least one epitopic site which is characteristic of FTLV. By characteristic, it is meant that the epitopic site will allow immunologic detection of the virus in a physiological sample with reasonable assurance. Usually, it will be desirable that the epitopic site be immunologically distinct from (i.e., not cross-reactive with antibodies which recognize) viruses other than FTLV. In some cases, however, it may be desirable that the epitopic site be immunologically similar to other viruses.

The FTLV polypeptides may be natural, i.e., including the entire FTLV protein or fragments thereof isolated from a natural source, or may be synthetic. The natural polypeptides may be isolated from the whole virus which is obtained as describe above by conventional techniques, such as affinity chromatography. Conveniently, polyclonal or monoclonal antibodies obtained according to the present invention (as described in more detail hereinbelow) may be used to prepare a suitable affinity column by well-known techniques. Such techniques are taught, for example, in Hudson and Hay, *Practical Immunology*, Blackwell Scientific Publications, Oxford, United Kingdom, 1980, Chapter 8.

Synthetic polypeptides which are immunologically cross-reactive with a natural FTLV protein may be produced by either of two general approaches. First, polypeptides having fewer than about 100 amino acids, more usually fewer than about 80 amino acids, and typically fewer than about 50 amino acids, may be synthesized by the well-known Merrifield solid-phase synthesis method where amino acids are sequentially added to a growing chain (Merrifield (1963) *J. Am. Chem. Soc.*, 85:2149–2156).

The second and preferred method for synthesizing the polypeptides of the present invention involves the expression in cultured cells of recombinant DNA molecules encoding a desired portion of the FTLV genome. The portion of the FTLV genome may itself be natural or synthetic, with natural genes obtainable from the isolated virus by conventional techniques. Of course, the genome of FTLV is RNA, and it will be necessary to transcribe the natural RNA into DNA by conventional techniques employing reverse transcriptase. Alternatively, polynucleotides may be synthesized by well-known techniques. For example, short single-stranded DNA fragments may be prepared by the phosphoramidite method described by Beaucage and Carruthers (1981), *Tett. Letters* 22:1859–1862. Double-stranded fragments may then be obtained either by synthesizing the complementary strand and then annealing the strands together under appropriate conditions, or by adding the complementary strand using DNA polymerase with an appropriate primer sequence.

The natural or synthetic DNA fragments coding for the desired FTLV protein or fragment may be incorporated in a DNA construct capable of introduction to and expression in in vitro cell culture. Usually, the DNA constructs will be suitable for replication in a unicellular host, such as yeast or bacteria. They may also be intended for introduction and integration within the genome of cultured mamalian or other eukaryotic cells. DNA constructs prepared for introduction into bacteria or yeast will include a replication system recognized by the host, the FTLV DNA fragment encoding the desired polypeptide product, transcriptional and translational initiation regulatory sequences joined to the 5'-end of the FTLV DNA fragment, and transcriptional and translational termination regulatory sequences joined to the 3'-end of the fragment. The transcriptional regulatory sequences will include a heterologus promoter which is recognized by the host. Conveniently, a variety of suitable expression vectors are commercially available for a number of hosts.

To be useful in the detection methods of the present invention, the polypeptides are obtained in a substantially pure form, that is, typically from about 50% W/W or more purity, substantially free of interfering proteins and contaminants. Preferably, the FTLV polypeptides are isolated or synthesized in a purity of at least 80% W/W, and more preferably, in at least about 95% W/W purity. Using conventional protein purification techniques, homogeneous polypeptide compositions of at least about 99% W/W purity can be obtained. For example, the proteins may be purified by use of the antibodies described hereinafter using the immunoabsorbant affinity columns described hereinabove.

Once a sufficient quantity of FTLV polypeptides have been obtained, polyclonal antibodies specific for FTLV may be produced by in vitro or in vivo techniques. In vitro techniques involved in vitro exposure lymphocytes to the antigenic polypeptides, while in vivo techniques require the injection of the polypeptides into a wide variety of vertebrates. Suitable vertebrates are non-human, including mice, rats, rabbits, sheep, goats, and the like. Polypeptides having more than about thirty amino acids, usually more than about fifty amino acids, may serve directly as the immunogen. If the polypeptide is smaller than about 10 kD, particularly less than about 6 kD, however, it may be necessary to join the polypeptide to a larger molecule to elicit the desired immune response. The immunogens are then injected into the animal according to a predetermined schedule, and the animals are bled periodicaly with successive bleeds having improved titer and specificity. Injections may be made intramuscularly, subcutaneously, or the like, and an adjuvent, such as incomplete Freund's adjuvent, will usually be employed. The whole virus can also be used as the immunogen, although selection of antibodies specific for a particular determinant will be more difficult.

If desired, monoclonal antibodies can be obtained by preparing immortalized cell lines capable of producing antibodies having the desired specificity. Such immortalized cell lines may be produced in a variety of ways. Conveniently, a small vertebrate, such as a mouse, is hyperimmunized with the desired antigen by the method just described. The vertebrate is then killed, usually several days after the final immunization, the spleen removed, and the spleen cells immortalized. The manner of immortalization is not critical. Presently, the most common technique is fusion with a myeloma cell fusion partner, as first described by Kohler and Milstein (1976) Eur. J. Immunol. 6:511–519. Other techniques include EBV transformation, transformation with oncogenes, retroviruses, etc., or any other method which provides for stable maintenance of the cell line and production of monoclonal antibodies.

When employing fusion with a fusion partner, the manner of fusion is not critical and various techniques may be employed. Conveniently, the spleen cells and myeloma cells are combined in the presence of a non-ionic detergent, usually polyethlene glycol, and other additives such as Dulbecco's Modified Eagle's medium, for a few minutes. At the end of the fusion, the non-ionic detergent is rapidly removed by washing the cells. The fused cells are promptly dispensed in small culture wells (usually in a microtiter plate at relatively low density, ranging from about one to $5\times10^5$ cells/well), in a selective medium chosen to support growth of the hybrid cells while being lethal to the myeloma cells. Usually, the myeloma cell line has been mutated to be sensitive to a lethal agent, typically being HAT sensitive, and the medium includes a HAT concentration sufficient to inhibit the proliferation of the unfused myeloma cells.

After sufficient time, usually from about one to two weeks, colonies of hybrids are observed and plates containing hyperpositive wells are identified. The plates and wells having only one colony per well are selected, and supernatants from these wells are tested for binding activity against FTLV or a particular FTLV protein. Once positive hybridomas are identified, the cell line can be maintained as a viable culture and/or a quantity of the virus may be grown out, separated, and stored by lyophilization.

Depending on the desired use for the antibodies, further screening of the hybridomas may be desirable. For use in immunodiagnostic assays, antibodies having very high specificity and affinity for the antigenic site are desirable.

Once the desired hybridomas have been selected, monoclonal antibodies may be isolated from supernatants of the growing colonies. The yield of antibodies obtained however, is usually low. The yield may be enhanced by various techniques, such as injection of the hybridoma cell line into the peritoneal cavity of a vertebrate host. Monoclonal antibodies may then be harvested from the ascites fluid or the blood. Proteinaceous and other contaminants will usually be removed from the monoclonal antibodies prior to use by conventional techniques, e.g., chromatography, gel filtration, precipitation, extraction, or the like.

The polypeptides and antibodies of the present invention may be used with or without modification for the detection of or vaccination against FTLV infection. Frequently, the polypeptides and antibodies will be labelled by joining, either covalently or non-covalently, a substance which provides for detectable signal. A wide variety of labels and conjugation techniques are known and are reported extensively in both the scientific and patent literature. Some of the labels include radionuclides, enzymes, substrates, cofactors, inhibitors, fluorescers, chemiluminescers, magnetic particles and the like. Patents teaching the use of such labels include U.S. Pat. Nos. 3,817,837; 3,850,752; 3,939,350; 3,996,345; 4,277,437; 4,275,149; and 4,366,241.

Antibodies and polypeptides prepared as described above can be used in various immunological techniques for detecting FTLV and anti-FTLV antibodies in physiological specimens, particularly body fluid samples, including blood, plasma, serum, urine, and the like, and cell samples, such as lymphocytes. Depending on the nature of the sample, both immunoassays and immunohistochemical staining techniques may find use.

Liquid phase immunoassays and Western blot analysis will find use in detection of FTLV in body fluids, particularly blood and urine. The use of antibodies in protein binding assays is well established. Numerous competitive and non-competitive protein binding assays have been described in the scientific and patent literature, and a large number of such assays are commercially available. Detailed methods for detecting the presence of the viruses in serum samples are set forth in the Experimental section hereinafter. Additionally, enzyme linked immunosorbent assays (ELISA) for detecting presence of antibodies to FTLV in blood are also set forth in the Experimental section.

Compositions of the present invention are also useful in preparing vaccines for protection against FTLV infection. For example, the whole virus may be wholly or partially inactivated. Partial inactivation may be achieved by passage at elevated temperatures or by contact with mutagens, such as ultraviolet light, ethyl methanesulfonate, and the like. Complete inactivation may be achieved by contact with other agents, including formalin, phenol, a-lactopropionate, ultraviolet light, heat, psorlens, platinum complexes, ozone and other viricidal agents.

The viral proteins and portions thereof, prepared as described above, may also be used in the preparation of subunit vaccines prepared by known techniques. Polypeptides displaying antigenic regions capable of eliciting protective immune response are selected and incorporated in an appropriate carrier. Alternatively, an antigenic portion of a viral protein or proteins may be incorporated into a larger protein by expression of fused proteins. The preparation of subunit vaccines for other viruses is described in various references, including Lerner et al. (1981) Proc. Natl. Acad. Sci. USA. 78:3403 and Bhatanagar et al. (1982) Proc. Natl. Acad. Sci. USA 79:4400. See also, U.S. Pat. Nos. 4,565,697 (where a naturally-derived viral protein is incorporated into a vaccine composition); 4,528,217 and 4,575,495 (where synthetic peptides forming a portion of a viral protein are incorporated into a vaccine composition). Other methods for forming vaccines employing only a portion of the viral proteins are described in U.S. Pat. Nos. 4,552,757; 4,552,758; and 4,593,002. The relevant portions of each of these cited references and patents are incorporated herein by reference.

The vaccines prepared as described above may be administered in any conventional manner, including oranasally, subcutaneously, or intramuscularly, except that oronasal administration will usually not be employed with a partially inactivated virus vaccine. Adjuvants will also find use with subcutaneous and intramuscular injection of completely inactivated vaccines to enhance the immune response.

Diagnostic tests for detecting the presence of FTLV in biological samples may also be performed using polynucleotide probes. Such polynucleotide probes may be prepared based on the sequence of the viral genome. The length of the probe is not critical, but will usually comprise at least about 12 bases, more usually comprising at least about 16 bases, which are substantially complementary to a portion of the viral genome. The probe itself may be DNA or RNA, and the probe need not have perfect complementarity with the FTLV genome, with one or two mismatched pairs being acceptable for probes up to 20 bases in length and three to five mismatched pairs in probes from 20 to 35 bases. The probes may be prepared synthetically, with suitable synthetic techniques having been described above, and will include a detectable label. Usually, the synthetic sequences are expanded in commonly available cloning vectors and suitable hosts in order to obtain large quantities. The expanded vectors may themselves be labelled for use as probes, or shorter fragments containing complementary strands may be excised and labelled. Methods for the preparation and utilization of nucleotide probes for diagnostic testing are described in U.S. Pat. No. 4,358,535 to Falkow et al., the disclosure of which is incorporated herein by reference.

A variety of labels have been employed, including those which have been described above for use in immunoassays, particularly radionuclides. Suitable labels may be bound to the probe by a variety of techniques. Commonly employed is nick translation with $\alpha$-$^{32}$P-dNTP terminal phosphate hydrolysis with alkaline phosphatase followed by 5'-end labelling with radioactive $^{32}$P employing $\lambda$-$^{32}$P-NTP and T4 polynucleotide kinase or 3'-end labelling with an $\alpha$-$^{32}$P-dNPT and terminal deoxynucleotidyl transferase Alternatively, nucleotides can be synthesized where one or more of the atoms present are replaced with a radioactive isotope, e.g., hydrogen with tritium. In addition, various linking groups can be employed. The terminal hydroxol can be esterified with inorganic acids, e.g., $^{32}$p phosphate or $^{14}$C organic acids, or else esterified with bifunctional reagents to provide other reactive groups to which labels can be linked.

The following examples are offered by way of illustration, not by way of limitation.

EXPERIMENTAL

Materials and Methods

1. Isolation and Culturing of FTLV

Peripheral blood lymphocytes (PBL) were isolated by Ficoll-Hypaque method (Boyam (1968) Scand. J. Clin. Lab. Invest. 97 (Suppl. 21):77) from 3–5 ml of heparinized blood of cats suspected of FTLV infection. The PBLs were resuspended in culture media at a final concentration of 0.5–1.0× $10^6$ cells/ml and placed in 25-cm$^2$ culture flasks. To this cell suspension, mitogen-stimulated normal donor PBLs were added at normal to infected PBL ratios of 1:1 or 1:2. Culture media consisted of RPMI 1640 with 10% heat-inactivated fetal calf serum, 10 mM HEPES, 100 U/ml penicillin, 10 µg/ml streptomycin, 50 µg/ml gentamycin, 2 mM L-glutamine, 5×10$^{-5}$M 2-mercaptoethanol, 2 µg/ml polybrene, and 100 U/ml human interleukin-2(IL-2). Cultures were incubated in 5% $CO_2$ at 37° C. and monitored routinely (every other day) for syncytia formation and other cytopathic effects (i.e., cell death). Culture supernatants were harvested for reverse transcriptase (RT) activity and cells were resuspended in fresh culture media on every 3rd day or twice a week. These cultures were further supplemented with stimulated normal PBLs from the same donor to maintain minimum cell concentration of 0.5–1.0×10$^6$ cells/ml. Such a procedure detected FTLV at as early as Day 5 and as late as Day 60 of the incubation period.

Virus production was monitored by syncytia formation and by reverse transcriptase (RT) assay using MG$^{++}$ as divalent cation, poly(rA)-oligo(dT$_{12-18}$) as template primer, and 5 µCi minimum of [3H]TTP per sample (Colche and Schlom (1980) Biochim. Biophys. Acta 607:445). Cultures with positive RT activities (two consecutive harvests with RT activity greater than 6,000 cpm/ml) were tested for the presence of FTLV antigen(s) on the cell surface or in the cells by immunofluorescence assay (IFA) with pooled FTLV-positive serum and for the presence of FTLV virions by electron microscopy. The cultures were considered positive for FTLV isolation when results from above assays all concur in the presence of a feline lentivirus. The virus isolates from such cultures were massively produced, purified by sucrose-gradient, and tested against FTLV isolate standard (Petaluma isolate) by Western blot analysis using pooled FTLV-positive serum. Those isolates showing one or more bandings comparable to FTLV standard are then considered FTLV isolates based on this antigenic comparison.

2. Isolation of FTLV From Other Specimen Samples

The procedures for specimen samples that are not PBLs were as follows. Cells from tissue specimen were teased and/or minced aseptically with forceps and scalpels, resuspended in culture media, and the procedures described for PBL samples are thereafter followed. Samples consisting of 0.5–1.0 ml of body fluids (i.e., serum, plasma, CNS fluid, saliva) were added to 5-ml cultures of stimulated donor PBL which was at $1 \times 10^6$ cells/ml, and the procedures described for PBL samples are thereafter followed.

3. Preparation of Stimulated PBLs from Normal Cat Donors

Specific-pathogen-free kittens and cats were used as normal donors of PBLs. Donor PBLs were prepared from heparinized blood (5–40 ml) by Ficoll-Hypaque method. The cells were resuspended in culture media (not supplemented with polybrene or human IL-2) and cultured in the presence of 5 μg/ml of concanavalin-A (Con A) in 5% $CO_2$ at 37° C. for three days. The stimulated donor PBLs were then harvested, washed with sterile 1× Hank's balanced salt solution, and resuspended in complete culture media ready to be used for FTLV isolation, or resuspended in culture media free of polybrene and recultured for later use. Stimulated PBLs could be grown for at least three months and used for FTLV isolation without loss in virus recovery. Other mitogens were successfully used to stimulate feline donor PBL for FTLV isolation, including Staphylococcal enterotoxin A (0.05 μg/ml), phytohemagglutinin (20 μg/ml), Staphylococcal protein A (5 μg/ml), and lipopolysaccharide (100 μg/ml).

4. Western Blot Analysis

A modification of the Western blot technique described by Carlson et al. (1985) J. Am. Med. Assn. 253:3405 was used. Sucrose-gradient purified virus was disrupted with 0.1% SDS and electrophoresed on a 8% preparative polyacrylamide slab gel (with 5% stacking gel) in presence of 0.1% sodium dodecyl sulfate (SDS). The separated viral proteins were transferred electrophoretically onto a nitrocellulose filter which was then treated with Buffer 3 containing 3% gelatin and cut into strips of identical size. Two lanes of each gel containing molecular weight standards were stained with amido black and later used for molecular weight comparison of the immunoblots.

Serum samples were diluted to 1:100 in Buffer 3 and incubated with blot strips in separate glass tubes for 60 min. at 37° C. The blot strips were washed individually and incubated with peroxidase-conjugated rabbit anti-cat IgG (Cappel Laboratories) at a dilution of 1:400 for 60 min. at 37° C. After extensive washing, each strip was incubated with a fresh substrate solution (0.05% diaminobenzidine and 0.01% $H_2O_2$ in 0.1M Tris, pH 7.4) for 4–10 min. at room temperature. The reaction was stopped with excess distilled $H_2O$ upon establishment of visible bands, and the strips are blot dried. The molecular weights of the bands on the immunoblots were then determined by comparing the migration distance with molecular standards from the original gel. Positive and negative control sera were included in each Western blot analysis as internal control for diagnostic evaluation.

5. Indirect Immunofluoresence Assay (IFA) for Detecting FTLV Antibodies and FTLV-Infected Cells Concanavalin A-simulated normal cat PBLs at a concentration of $2 \times 10^6$ cells/ml in culture media were infected with FTLV at RT levels of 5,000–10,000 cpm/ml and incubated in 5% $CO_2$ at 37° C. The culture media used throughout these studies consisted of RPMI-1640 media containing 100 U/ml rIL-2, 2 fg/ml polybrene, 10% heat-inactivated FCS, 1× penicillin/streptomycin, 50 μg/ml gentamycin, $5 \times 10^{-5}$M 2-mercaptoethanol, and 10 mM Hepes. The virus stocks were infected tissue culture fluid (TCF) (greater than 100,000 cpm/ml in RT activity) which were filtered (0.45 μm), aliquoted, and stored frozen at −70° C. The culture fluids were harvested every 3–4 days, and the infected cells were recultured in a fresh culture media and supplemented with stimulated normal cat PBL to maintain the live cell density of $2 \times 10^6$ cells/ml. Virus from the infected TCF was purified by sucrose gradient method (Pedersen et al. (1987) Science 235:790), and used as antigens for ELISA and Western blot. Equal number of infected PBLs from Day 3, 6, 9, 12, and long-term cultures from above were pooled, washed with phosphate buffered saline (PBS), air-dried on 10-well IFA slides at $5 \times 10^6$ cells/ml, acetone-fixed for 10 min and stored at −5° C. in a desicator. These slides were thawed to room temperature just prior to IFA testing. Fifteen μl of 1:10 diluted sera were placed on individual wells and incubated for additional 30 min at 37° C. with fluorescein-conjugated anti-cat IgG (Antibodies Incorporated, Davis, Calif.) at a dilution of 1:75. After washing, the slides were counterstained with 0.01% evans blue, mounted in buffered glycerol, and read by fluorescent microscopy. The serum samples were considered positive for FTLV antibodies when both giant cells and infected cells gave typical membrane and cytoplasmic fluorescence. Positive and negative control serum were included in every assay.

6. Enzyme-Linked Immunosorbent Assay (ELISA) for Detecting FTLV Antibodies

ELISA used in this study was a modification of the methods described by Lutz et al. (1980) Cancer Res. 40:364 for FeLV and Carlson et al. (1985) supra for HIV. Sodium dodecylsulfate (0.1% SDS)-disrupted purified FTLV were diluted in coating buffer (0.1M $NaHCO_3$, pH 9.6) to 2 μg/ml, and 0.1 ml (200 ng) of this viral suspension was added to each well of the Immulon II microtiter plates. The plates were incubated for 12 to 16 hrs. at 37° C., and then washed with wash solution (0.05%-Tween-20, 0.15M NaCl). The test sera were diluted 1:100 in Buffer 3 (0.15M NaCl, 1 mM edetic acid, 0.05% Tween-20, 0.1% bovine serum albumin, pH 7.4), and 0.1 ml of the diluted sera were added to each well in duplicate and incubated for 60 min. at 37° C. The plates were then washed and incubated with 1:100 dilution of peroxidase-conjugated rabbit anti-cat IgG (Cappel Laboratories, Conchranville, Pa.) for 30 min at 37° C. After another wash cycle, the plates were incubated with a fresh substrate solution (50 mM citric acid adjusted to pH 4.0, 0.2 mM 2, 2'-azinobis-3-ethylbenzthiazoline-sulfonic acid, 2 mM $H_2O_2$) for 10 min. at room temperature. The reaction was stopped with the addition of 0.1 ml of 0.2M hydrogen fluoride and the absorbance at 405 nm was measured by an ELISA plate reader. Each ELISA plate contains duplicate wells of positive and negative control sera which were used throughout the study as internal standards for diagnostic comparison.

7. Preparation of Inactivated Purified FTLV as a Whole Virus Vaccine Against FTLV Tissue culture fluid (TCF) infected with FTLV was centrifuged at 3,000 rpm for 1 hr. to remove cellular debris, and the cell-free TCF was pelleted at 17,000 rpm for 2 hrs. The pelleted virus is then layered on a 10/50% (W/V) continuous sucrose gradient in TEN buffer tris-base(pH 7.4) containing 0.1M NaCl and 1 mM EDTA and ultracentrifuged in a Beckman SW41 rotor for 3 hrs. at 36,000 rpm (Pedersen et al. (1987) Supra). Peak viral fractions of the gradient were determined by the presence of reverse transcriptase activity, and the peak fractions pooled, diluted with TEN buffer, and pelleted out of the sucrose solution at 17,000 rpm for 2 hrs. The resulting purified virus were inactivated by psoralen (Marx et al. (1986) J. Virol. 60:431) and then by 0.8% formaldehyde at 4° C. for 24 hrs. (Swansstrom et al. (1981) Virology 113:613). The inactivated virus was pelleted out of the formaldehyde solution, resuspended in saline solution, and mixed with adjuvant (N-acetylmuramyl-L-alanine-D-isoglutamine, MDP) before inoculation.

RESULTS

1. Initial Isolation and Serial Transmission of FTLV

FTLV was isolated from a cattery of 43 cats which were all seronegative for FeLV. A number of cats in one pen had died, and several had an immunodeficiency-like syndrome. Only one of 18 symptom free cats in the cattery showed serologic evidence of FTLV infection (by IFA), while ten of 25 cats showing signs of ill health were seropositive for the virus by IFA. The disease course and clinical signs observed in these ten cats (which died over a four-year-period) are set forth in Table 1.

TABLE I

| Cat Name | Duration of Illness | Clinical Signs |
|---|---|---|
| Cv | 3 years | Chronic rhinitis, conjunctivitis, diarrhea, abortion, vague neurologic abnormalities, periodontitis, gingivitis, anemia, emaciation |
| GK | 7 months | Chronic rhinitis, diarrhea, perodonitis, gingivitis, anemia, emaciation |
| FL[1] | 9 months | Diarrhea, hematochezia, periodontitis, gingivitis, alopecia, seborrheic dermatitis, emaciation |
| SA[1] | 7 months | Found extremely dehydrated, depressed and near death. Responded well to treatment but fell into a pattern of depression, dehydration and weight loss. Severe diarrhea for the last 2 weeks of life. |
| TC[1] | 6 months | Found near death and died 5 hours later. Appeared healthy the night before. History of periodontitis and gingivitis for several months prior to death. Evidence of severe chronic and acute enteritis at necropsy. |
| CY | hours | Found dead. Appeared healthy the night before. Possible acute enteritis. |
| RU | hours | Found dead. Appeared healthy the night before. Possible acute enteritis. |
| BL | 1 month | Chronic diarrhea, anorexia, dehydration, emaciation. |

TABLE I-continued

| Cat Name | Duration of Illness | Clinical Signs |
|---|---|---|
| CH[2] | 1 month | Thin, seborrheic dermatitis, chronic rhinitis, anemia. |
| CL | 5 months | Found depressed and hypothermic with terminal hysteria and rage. |

[1]The new retrovirus was isolated from blood of cat FL and from pooled plasma from cats SA and TC.
[2]Tested positive for FTLV BY IFA prior to death. All other cats died before testing for FTLV.

An FTLV strain designated feline T-lymphotropic lentivirus, Petaluma isolate, was deposited at the American Type Culture Collection, Parklawn Drive, Rockville, Md. 20852, on Aug. 5, 1987 and granted Accession No. VR 2186.

Given the possible infectious nature of the disease syndrome, an attempt was made to serially transmit the disease from affected cattery cats to specific pathogen-free (SPF) kittens. Whole blood (1 ml) from cat FL was inoculated intraperitoneally into SPF kitten 2428. A second SPF kitten (2429) was inoculated intraperitoneally with 2 ml of filtered (0.22 fM) pooled plasma from cats SA and TC. Plasma from these donor cats was used instead of blood because both of them tested positive for FeSFV infection. FeSFV is highly cell-associated and very little virus occurs free in plasma. Plasma buffy coat preparations, and bone marrow samples from cats FL and SA were also cocultivated with Fc9, Fcwf-4, and Crfk feline fibroblasts. Cultures were monitored for cytopathic effect (CPE), $Mg^{+2}$- and $Mn^{-2}$-dependent reverse transcriptase (RT) activity, and FeLV-p27 antigen expression by ELISA. The cocultures with plasma and buffy coat cells were discarded after they were negative for 6 weeks. Bone marrow cultures from cat SA yielded FeSFV after several passages but were negative when examined by transmission electron microscopy for other agents.

Kittens 2428 and 2429 were monitored daily for clinical signs of illness and complete blood counts were taken weekly. A generalized enlargement of peripheral lymph nodes was noticed beginning 4 weeks after inoculation. A low-grade fever appeared 2 weeks later and was associated with a precipitous drop in the total leukocyte count and absolute numbers of polymorphonuclear neutrophils. Platelet and red blood cell counts remained normal, however. Cat 2429 developed a severe bacterial cellulitis at the site of ear tagging, septicenia, and high fever within a week of the time that the white cell count decreased. The infection and high fever disappeared after broad spectrum antibiotic therapy was instituted. The leukopenia and low-grade fever disappeared after 2 to 4 weeks, but the generalized lymphadenopathy persisted for at least 5 months after inoculation.

Buffy coats were prepared from blood samples collected from the two experimentally inoculated kittens (2428 and 2429) during the leukopenic phase of their illness. The buffy coats were cocultured with stimulated peripheral blood lymphocytes (PBL) from normal SPF cat donors. The donor lymphocytes were harvested from fresh whole blood by means of Ficoll-Hypaque gradients and were stimulated with concanavalin A (Con A; 5 μg,/ml). Three days after Con A stimulation, nonadherent blood leukocytes were transferred to fresh flasks and further stimulated with recombinant human interleukin-2 (IL-2; 100 U/ml). Cells examined after 7 days in culture were more than 95% T lymphocytes as determined by an IFA with the use of rabbit antiserum to feline theta, immunoglobulin G (IgG), and immunoglobulin M (IgM) antigens. Cultures were replenished with fresh Con A and IL-2-stimulated PBL every 5 to 7 days. A cytopathic effect (CPE) consisting of ballooning degeneration, increased cell death, and giant cell formation was noted in cultures of cells from cat 2429 within 14 to 21 days of cocultivation. A similar CPE was seen in cultures from cat 2428 after 4 to 6 weeks. Cytopathic changes were associated with the appearance of RT activity that was totally $Mg^{2-}$-dependent. The RT activity of FTLV resembled that of the HIV and differed from that of FeLV (FIGS. 1A–1C). Lymphoid cell cultures showing CPE and RT activity were negative for FeLV-p27 antigen by ELISA and for FeSFV by IFA. Transmission electron micrographs of RT and CPE-positive cultures revealed mature, immature, and budding particles typical of lentiviruses (FIG. 2). The particles were slightly smaller and ellipsoid than HIV and had more prominent envelope spikes. Particles with the morphology of type C or D oncornaviruses or FeSFV were not observed. Virus purified from feline T-lymphoid cultures banded at a density of 1.15 $g/cm^3$ in continuous sucrose gradients (FIG. 3).

Reverse transcriptase levels in culture supernatants increased progressively after each serial passage of the virus in fresh PBL and peaked after day 40 to 45. After exposure of fresh PBL with infected cell-free culture supernatants, the RT level in the culture increase progressively and peaked by day 7. Infectivity for T-lymphocyte enriched PBL could be readily demonstrated with both filtered tissue culture fluid and cellular inocula. The virus readily infected FL-74 and LSA-I cell lines, both of which are feline T-lymphotropic cell lines chronically infected with FeLV. The virus failed to replicate, however, in several feline, fibroblastic cell lines, including Fc9, Fcwf-4, and Crfk. Infectivity studies with long-term human T-lymphoid cell lines (H9, HUT 78) and with primary cultures of human PBL stimulated with phytohemagglutinin and IL-2 have been negative.

The serologic relation between FTLV and HIV was examined. Serum samples from all 43 cats were uniformly negative against HIV when tested by IFA and Western blotting. Western blots, prepared from gradient-purified virus from cat 2429 or from virus-infected cell lysates, reacted with sera from experimentally infected cat 2429 and with several cats from the cattery, but not with pooled human sera positive for HIV. Three humans who had persistent and close contact with cats in the cattery had no antibodies to HIV or to the new feline virus by IFA and Western blotting.

A serologic survey of the cattery was conducted by using an IFA with infected feline lymphocytes as the substrate. Most of the infected animals were confined to one pen, with only two infected animals found in other pens. A thorough physical examination of all 43 cats in the cattery showed that 18 were healthy and 25 had various ailments. Unhealthy cats were either very thin and rough-coated or had one or more of a number of chronic infections including gingivitis, periodontitis, pustular dermatitis, ear infections, chronic rhinitis, chronic conjunctivitis, or diarrhea. Only 1 of the 18 (5.6%) healthy cats was seropositive for the new virus, whereas 10 of the 25 (40%) unhealthy cats had antibodies to the new virus. None of the cats were infected with FeLV; however, several were seropositive for FeSFV and feline infectious peritonitis virus (FIPV).

Clinical signs observed in the ten cats that were seropositive for the new virus included chronic rhinitis, excessive thinness, and anemia. One of these animals had a recurrent bacterial cystitis that is uncommon in cats. Periodontitis, stomatitis, gingivitis, miliary pustular dermatitis, bacterial otitis exema, and aural hematomas were recognized in both seropositive and seronegative animals. Neurologic abnormalities were not observed in any of the surviving seronegative or seropositive cats; they were recognized, however, in two cats that had died prior to the institution of testing for the new virus (Table 1).

A disease identical to that transmitted to SPF kittens 2428 and 2429 inoculated with whole blood or plasma was subsequently transmitted to other SPF kittens by means of purified virus that had been propagated in tissue culture. The cultured virus was then reisolated from the blood of these kittens several weeks later. An identical virus was also repeatedly reisolated from cats 2428 and 2429 over a period of 4 months or more, thus indicating the persistence of the infection. A limited serologic survey of cats has confirmed the existence of the new virus in diseased cats from many different geographic areas of Northern California, as well as in other states. Seropositive cats have also been identified in Canada and Japan.

Although the foregoing invention has been described in some detail by way of illustration and example for purposes of clarity of understanding, it will be obvious that certain changes and modifications may be practiced within the scope of the appended claims.

What is claimed is:

1. An enzyme-linked immunosorbent assay (ELISA) for detecting Feline Immunodeficiency Virus (FIV) antibodies, said assay comprising:

a solid phase coated with FIV antigen, wherein FIV antibodies in a sample exposed to the solid phase will bind to the antigen; and a detectable label conjugate which will bind to FIV antibodies bound to the solid phase.

2. An ELISA as in claim 1, wherein the solid phase is coated with sodium dodecylsulfate-disrupted purified FIV.

3. An ELISA as in claims 1 or 2, wherein the solid phase is a microtiter well.

4. An ELISA as in claim 1, wherein the conjugate comprises anti-cat antibody.

5. An ELISA as in claim 1 or 4, wherein the conjugate comprises an enzyme.

6. An ELISA as in claim 5, wherein the enzyme is horse radish peroxidase.

7. An ELISA as in claim 5, further comprising a substrate for the enzyme

8. An apparatus for capturing FIV antibodies from a liquid sample, said apparatus comprising a solid phase coated with FIV antigen, wherein FIV antibodies in a sample exposed to the solid phase will bind to the antigen.

9. An apparatus as in claim 8, wherein the solid phase is coated with sodium dodecylsulfate-disrupted purified FIV.

10. An apparatus as in claim 8, wherein the solid phase is a microtiter well.

* * * * *